United States Patent
Kim et al.

(10) Patent No.: US 11,202,749 B2
(45) Date of Patent: Dec. 21, 2021

(54) COMPOSITION FOR SKIN AGING MEASUREMENT, PREVENTION, OR ALLEVIATION, USING HAPLN1

(71) Applicant: HAPLNSCIENCE INC., Gyeonggi-do (KR)

(72) Inventors: Dae Kyong Kim, Gyeonggi-do (KR); Zhicheng Fu, Henan (CN); Moon Jung Back, Seoul (KR)

(73) Assignee: HAPLNSCIENCE INC., Gyeonggi-do (KR)

( * ) Notice: Subject to any disclaimer, the term of this patent is extended or adjusted under 35 U.S.C. 154(b) by 0 days.

(21) Appl. No.: 16/562,633

(22) Filed: Sep. 6, 2019

(65) Prior Publication Data

US 2020/0000700 A1    Jan. 2, 2020

Related U.S. Application Data

(63) Continuation of application No. PCT/KR2017/002395, filed on Mar. 6, 2017.

(51) Int. Cl.

| A61K 8/64 | (2006.01) |
| A61K 8/73 | (2006.01) |
| A61Q 19/08 | (2006.01) |
| C12Q 1/6883 | (2018.01) |
| G01N 33/50 | (2006.01) |
| G01N 33/68 | (2006.01) |

(52) U.S. Cl.
CPC ............... *A61K 8/64* (2013.01); *A61K 8/735* (2013.01); *A61Q 19/08* (2013.01); *C12Q 1/6883* (2013.01); *G01N 33/502* (2013.01); *G01N 33/6881* (2013.01); *C12Q 2600/148* (2013.01); *C12Q 2600/158* (2013.01)

(58) Field of Classification Search
None
See application file for complete search history.

(56) References Cited

U.S. PATENT DOCUMENTS

| 7,908,090 B2 | 3/2011 | Kim et al. |
| 2008/0051680 A1 | 2/2008 | Luebcke |
| 2009/0220488 A1 | 9/2009 | Gardner |
| 2014/0163118 A1* | 6/2014 | Giuliani ............... A61Q 19/08 514/789 |
| 2015/0133328 A1 | 5/2015 | Ikuta et al. |
| 2016/0192689 A1 | 7/2016 | Horn |

FOREIGN PATENT DOCUMENTS

| EP | 2924432 A1 | 9/2015 |
| KR | 10-2017-0031060 A | 3/2017 |
| RU | 2388504 | 5/2010 |
| WO | WO 2013/129456 A1 | 9/2013 |
| WO | WO 2016/156788 A1 | 10/2016 |

OTHER PUBLICATIONS

Makrantonaki et al. "Genetics and skin aging" Demato-Endocrinology 4:280-284. (Year: 2012).*
Ganceviciene et al. "Skin anti-aging strategies" Demato-Endocrinology 4:308-319. (Year: 2012).*
Kaur et al. "Remodeling of the Collagen Matrix in Aging Skin Promotes Melanoma Metastasis and Affects Immune Cell Motility" Cancer Discovery 9:64-81. (Year: 2018).*
International Search Report and Written Opinion for Application No. PCT/KR2017/002395 dated Nov. 27, 2017, 12 pages.
Poetschke, J. et al., "Anti-wrinkle Creams with Hyaluronic Acid: How Effective Are They?", MMW-Fortschritte der Medizin, May 25, 2016, vol. 158, Suppl. 4, pp. 1-6 See page 6.
Végh M. J. et al., Hippocampal Extracellular Matrix Levels and Stochasticity in Synaptic Protein Expression Increase with Age and Are Associated with Age-dependent Cognitive Decline, Molecular & Cellular Proteomics, pp. 2975-2985, vol. 13(11), American Society for Biochemistry and Molecular Biology, Inc., 2014.
Govindan et al., "Hapln1a is Required for Connexin43-Dependent Growth and Patterning in the Regenerating Fin Skeleton," *PLoS One*, vol. 9, No. 2, e88574, 2014 (10 pages).
Ivanova et al., "Protumorigenic Role of HAPLN1 and its IgV Domain in Malignant Pleural Mesothelioma," *Clin Cancer Res*, 15(8), 2602-2611, 2009.

* cited by examiner

*Primary Examiner* — Sudhakar Katakam
*Assistant Examiner* — Zachary J Miknis
(74) *Attorney, Agent, or Firm* — Klarquist Sparkman, LLP

(57) ABSTRACT

The present disclosure relates to HAPLN1 protein of an aged individual. The HAPLN1 protein exhibits reduced expression with aging, and when administered, its effect in alleviating and reversing skin aging including wrinkles is excellent. Therefore, by exploiting the difference in expression, provided are a biomarker composition for measuring skin aging, capable of diagnosing skin aging; a kit; and a method of screening for skin aging alleviating agents, comprising detecting the expression level of HAPLN1 protein or HAPLN1 gene. In addition, provided are a pharmaceutical composition, cosmetic composition, or health functional food for preventing or alleviating skin aging, and a cosmetic composition or health functional food for alleviating wrinkles, each containing any one or more selected from the group consisting of HAPLN1 protein, a gene encoding the same, and an effective agent for promoting the expression or activating the functions of HAPLN1 protein or gene.

7 Claims, 21 Drawing Sheets

Young  Old

COMPOSITION FOR SKIN AGING MEASUREMENT, PREVENTION, OR ALLEVIATION, USING HAPLN1

RELATE APPLICATIONS

This application is a continuation of PCT Application No. PCT/KR2017/002395, filed Mar. 6, 2017, which is hereby incorporated in its entirety by reference as set forth herein.

TECHNICAL FIELD

The present disclosure relates to a biomarker composition for measuring skin aging using hyaluronan and proteoglycan link protein 1 (HAPLN1), and a pharmaceutical composition for preventing or alleviating skin aging, cosmetic composition, or health functional food.

BACKGROUND ART

One of the most obvious symptoms of skin aging is a decrease in dermal extracellular matrix, causing wrinkles. An extracellular matrix of the dermal layer includes various proteins, such as collagen, elastin, and glycoprotein, as main components. Among these proteins, collagen accounts for over 90% and about 90% of the collagen is type I collagen. About 70% of the reduction in the amount of type I collagen caused by aging was identified in the dermal extracellular matrix.

Hyaluronic acid, which is a polysaccharide consisting of amino sugars and uronic acid is distributed in all tissues of the living body and about 50% of the total amount in the body is distributed in the skin. Hyaluronic acid may bind up to 1000 times its mass in water and fills the extracellular matrix of dermal tissue. In addition, hyaluronic acid may form aggregates of various glycoproteins and proteoglycans to store or preserve various growth factors therein. According to clinical trial results, hyaluronic acid increases proliferation of dermal fibroblasts, production of collagen, and secretion of growth factors, and it is known that hyaluronic acid levels decrease by more than 40% with age.

Skin aging takes place in two ways: intrinsic aging and extrinsic aging. Extrinsic skin aging is mainly caused by external environmental factors such as ultra-violet light (UV) and smoking, and intrinsic skin aging is associated with age. Although at present various methods, e.g., use of UV-blocking cosmetics, have been reported for preventing extrinsic skin aging, methods for preventing intrinsic aging have not been developed yet. Therefore, efforts to prevent or alleviate intrinsic skin aging are required.

SUMMARY

Technical Problem

Provided is a biomarker composition for measuring skin aging.

Provided is a kit for measuring skin aging.

Provided is a method of screening for a skin aging alleviating agent.

Provided is a pharmaceutical composition for preventing or alleviating skin aging.

Provided is a cosmetic composition for preventing or alleviating skin aging or a cosmetic composition for alleviating wrinkles.

Provided is a health functional food for preventing or alleviating skin aging or a health functional food for alleviating wrinkles.

Solution to Problem

According to an aspect of the present disclosure, a biomarker composition for measuring skin aging, the biomarker composition including an agent for detecting hyaluronan and proteoglycan link protein 1 (HAPLN1) protein or HAPLN1 gene from a biological sample is provided.

Also, according to another aspect of the present disclosure, a kit for measuring skin aging, the kit including an agent for detecting HAPLN1 protein or HAPLN1 gene from a biological sample is provided.

Also, according to another aspect of the present disclosure, a method of screening for a skin aging alleviating agent, the method including: incubating a biological sample with a compound; detecting an expression level of HAPLN1 protein or gene from the biological sample; and comparing the expression level with an expression level of the same protein or gene in a normal control not incubated with the compound is provided.

Also, according to another aspect of the present disclosure, a pharmaceutical composition for preventing or alleviating skin aging, the pharmaceutical composition including at least one selected from the group consisting of HAPLN1 protein, a gene coding for the HAPLN1 protein, and an effective agent for promoting the expression or activating the functions of HAPLN1 protein or gene, as an active ingredient, is provided.

Also, according to another aspect of the present disclosure, a cosmetic composition for preventing or alleviating skin aging or a cosmetic composition for alleviating wrinkles, each including HAPLN1 protein or an effective agent for promoting the expression or activating the functions of HAPLN1 protein, as an active ingredient, is provided.

Also, according to another aspect of the present disclosure, a health functional food for preventing or alleviating skin aging or a health functional food for alleviating wrinkles, each including HAPLN1 protein or an effective agent for promoting the expression or activating the functions of HAPLN1 protein, as an active ingredient, is provided.

The pharmaceutical composition, the cosmetic composition, or the health functional food may further include hyaluronic acid.

Advantageous Effects of Disclosure

According to the present disclosure, the HAPLN1 protein has reduced expression in an aged individual and has an excellent effect of alleviating and reversing skin aging including wrinkles when administered. Therefore, the present disclosure may effectively provide a biomarker composition and a kit for measuring skin aging, each capable of diagnosing skin aging and including an agent detecting HAPLN1 protein or HAPLN1 gene, a method of screening for an agent preventing or alleviating skin aging, the method including detecting an expression level of HAPLN1 protein or HAPLN1 gene, a pharmaceutical composition, cosmetic composition, or health functional food for preventing or alleviating skin aging, and a cosmetic composition or health functional food for alleviating wrinkles.

DETAILED DESCRIPTION OF EMBODIMENTS

Figure 1A:
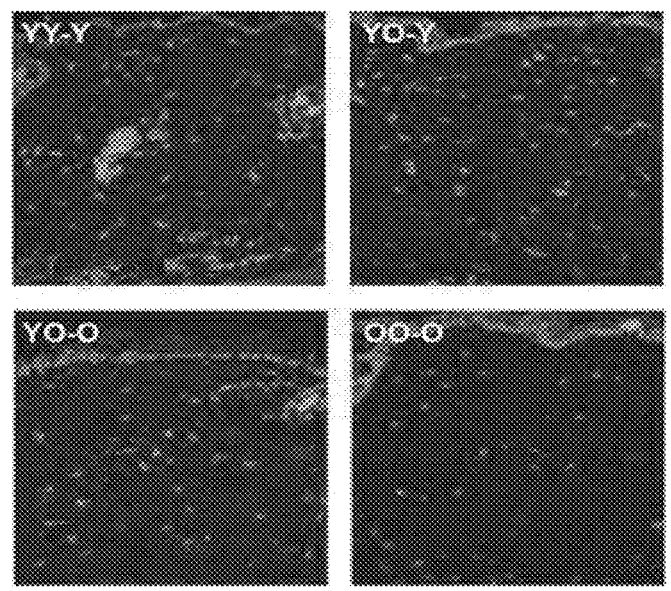
FIGS. 1A and 1B show results of identifying collagen production in a heterochronic parabiotic pair of an old mouse O and a young mouse Y.
Figure 1B:
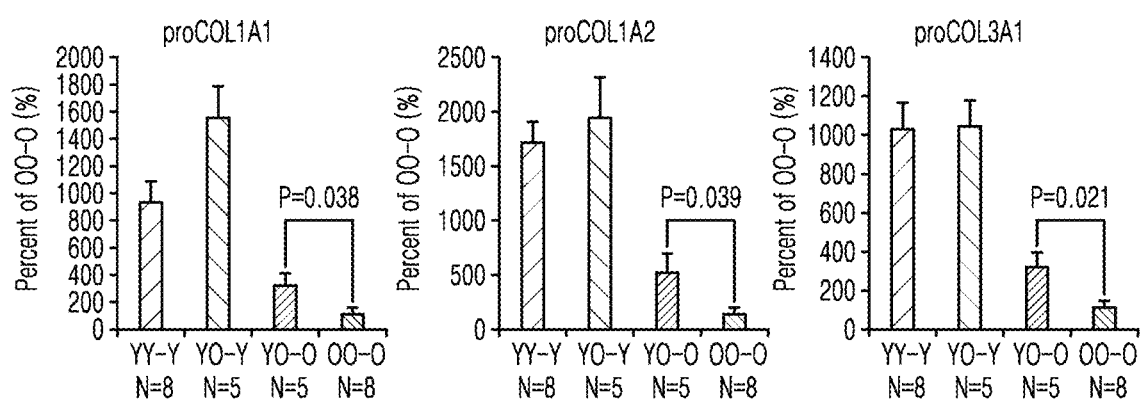
Figure 2A:
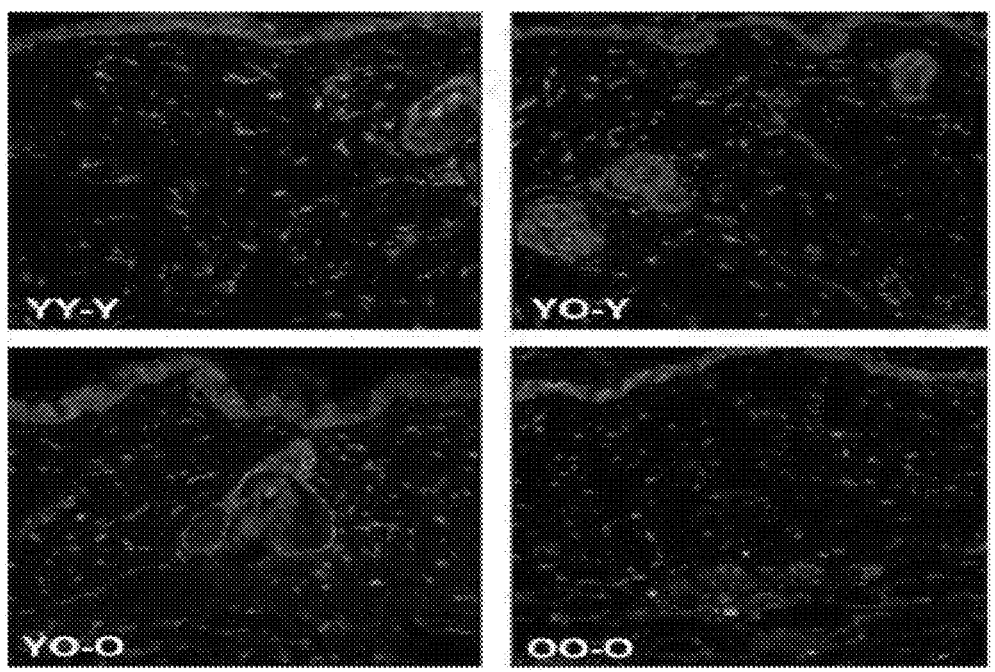
FIGS. 2A and 2B show results of identifying hyaluronic acid (HA) levels of respective old mouse (YO-O) and young mouse (YO-Y) in a heterochronic parabiotic pair of an old mouse O and a young mouse Y; HA level of young mouse (YY-Y) in a heterochronic parabiotic pair of a young mouse Y and a young mouse Y; and HA level of old mouse (OO-O) in a heterochronic parabiotic pair of an old mouse O and an old mouse O.
Figure 2B:
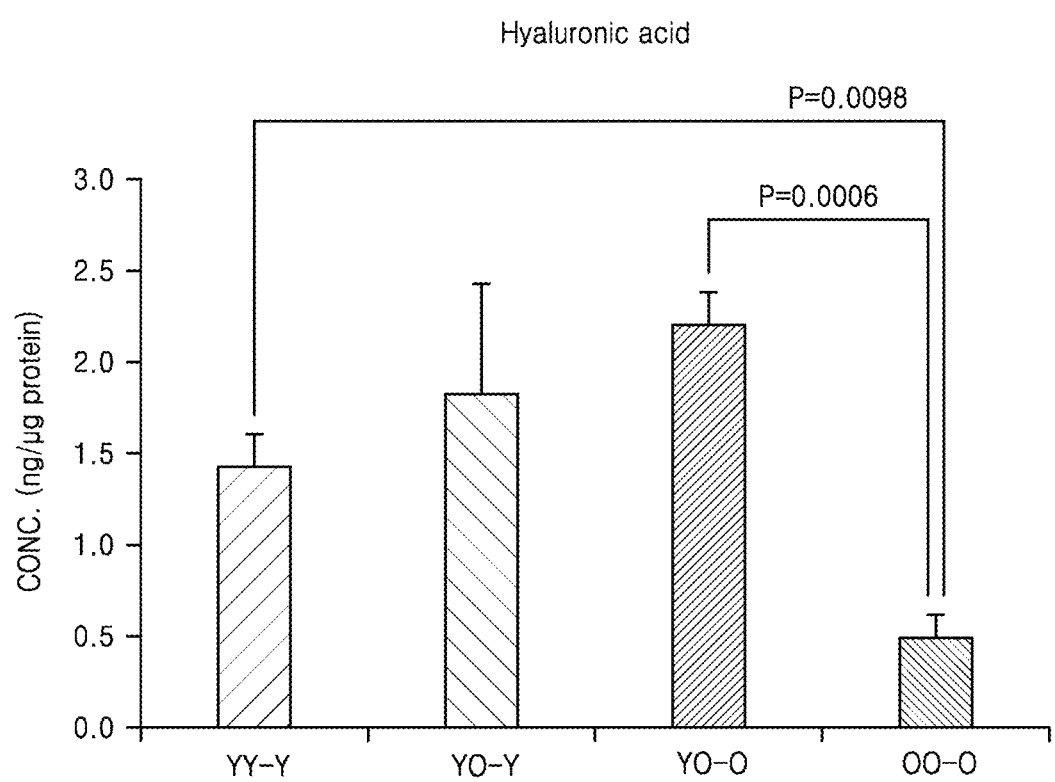

The present inventors have found that expression levels of hyaluronan and proteoglycan link protein 1 (HAPLN1) decrease in the old mice by comparing protein expression levels between old mice and young mice, thereby completing the present invention. HAPLN1 is a protein that stabilizes hyaluronic acid by linking hyaluronic acid to proteoglycan and effects of HAPLN1 on alleviating skin aging have not been reported to date.

The present disclosure provides a biomarker composition for measuring skin aging, the biomarker composition including an agent for detecting HAPLN1 protein or HAPLN1 gene from a biological sample.

The HAPLN1 protein may be mouse HAPLN1 (NCBI accession: NP_038528.3, Gene ID:12950) or human HAPLN1 (NCBI accession: AAH57808.1, Gene ID: 1404), without being limited thereto.

The agent may include, but is not limited to, at least one selected from an antibody, an antisense RNA, an aptamer, and a compound.

The skin aging may include wrinkles caused by a decrease in dermal extracellular matrix of skin.

The present disclosure also provides a kit for measuring skin aging, the kit including an agent for detecting HAPLN1 protein or HAPLN1 gene from a biological sample.

The agent may include, but is not limited to, at least one selected from an antibody, an antisense RNA, an aptamer, and a compound.

The antibody is a polyclonal antibody or a monoclonal antibody.

The polyclonal antibody may be prepared by injecting a protein expressed by the gene or a fragment thereof into a host as an immunogen according to any method known in the art. The host may include a mammal such as a mouse, a rat, a sheep, or a rabbit. The immunogen is injected intramuscularly, intraperitoneally, or subcutaneously and usually administered with an adjuvant for improving antigenicity. Serum may be periodically collected from the host to obtain serum having increased titer and antigen specificity and purify an antibody therefrom.

The monoclonal antibody may be prepared by a technique of producing immortalized cell lines via fusion well known in the art. For example, a mouse may be immunized by a protein expressed by the gene or synthetic peptide conjugated with bovine serum albumin. Antigen-producing B lymphocytes isolated from a mouse are fused with human or mouse myeloma cells to prepare immortalized hybridoma cells. Production of a monoclonal antibody is identified by analyzing the hybridoma cells using indirect enzyme-linked immunoabsorbent assay (ELISA). A positive clone may be selected and cultured and an antibody may be isolated therefrom and purified. Alternatively, the positive clone may be intraperitoneally injected into rats and ascites may be obtained therefrom to obtain a monoclonal antibody.

In general, the monoclonal antibody may be quantitively analyzed by color reaction using a secondary antibody conjugated with an enzyme such as alkaline phosphatase (AP) or horseradish peroxidase (HRP) and a substrate thereof or quantitively analyzed using the AP or HRP directly conjugated with the monoclonal antibody of the protein.

The reaction between the protein and the antibody may be identified by protein identification experiments such as western blotting, immunoprecipitation (IP), enzyme-linked immunoabsorbent assay (ELISA), and immunohistochemistry (IHC), without being limited thereto.

A kit including the antibody may generally include a lyophilized antibody and a buffer, a stabilizer, an inactivated protein, or the like, and the antibody may be labeled with a radionuclide, a fluorescent dye, an enzyme, or the like.

The present disclosure also provides a method of screening for a skin aging alleviating agent, the method including: incubating a biological sample with a compound; detecting an expression level of HAPLN1 protein or gene from the biological sample; and comparing the expression level with an expression level of the same protein or gene in a normal control not incubated with the compound.

The biological sample may include at least one selected from tissue, cells, whole blood, serum, and plasma.

The present disclosure also provides a pharmaceutical composition for preventing or alleviating skin aging, the pharmaceutical composition including at least one selected from the group consisting of HAPLN1 protein, a gene coding for the HAPLN1 protein, and an effective agent for promoting the expression or activating the functions of HAPLN1 protein or gene, as an active ingredient.

The pharmaceutical composition may further include hyaluronic acid (HA).

The pharmaceutical composition may be provided in one or more formulations selected from the group consisting of gels, emulsions, injections, powders, granules, aerosols, pastes, percutaneous absorbers, and patches according to a conventional method, but is not limited thereto.

According to another example embodiment, the pharmaceutical composition may further include at least one additive selected from the group consisting of suitable carriers, excipients, disintegrants, sweeteners, coatings, swelling agents, lubricants, glidants, flavoring agents, antioxidants, buffers, bacteriostats, diluents, dispersants, surfactants, and binders that are commonly used in preparation of pharmaceutical compositions.

Specifically, the carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, and mineral oil. Solid formulations for oral administration may include tablets, pills, powders, granules, capsules, and the like, and the solid formulations may be prepared by mixing at least one excipient, such as starch, calcium carbonate, sucrose, lactose, or gelatin with the composition. Lubricants such as magnesium stearate and talc may also be used in addition to a simple excipient. Liquid formulation for oral administration may be suspensions, formulations for internal use, emulsions, syrups, or the like, and may include various excipients such as humectants, sweeteners, fragrances, and preservatives in addition to simple common diluents such as water and liquid paraffin. Formulations for parenteral administration may include sterile aqueous solutions, non-aqueous solvents, suspensions, emulsions, lyophilizates, suppositories, and the like. The non-liquid solutions and suspensions may be propylene glycol, polyethylene glycol, vegetable oils such as olive oil, injectable esters such as ethyl oleate, or the like. Bases for the suppositories may include WITEPSOL, Macrogol, TWEEN 61, cacao butter, laurin butter, glycerogelatin, or the like.

Dosage of the HAPLN1 protein and the effective agent may vary according to conditions and weight of a subject, type and degree of aging, formulation of a drug, route of administration, and duration of administration and may be appropriately adjusted by those of ordinary skill in the art.

As used herein, the term 'subject' may be a mammal including a human, without being limited thereto.

The present disclosure also provides a cosmetic composition for preventing or alleviating skin aging including HAPLN1 protein or an effective agent for promoting the expression or activating the functions of HAPLN1 protein, as an active ingredient.

The cosmetic composition may further include hyaluronic acid.

The cosmetic composition may further include common adjuvants such as stabilizers, solubilizers, vitamins, pigments, and fragrances, and carriers in addition to the HAPLN1 protein and the effective agent that are the active ingredients.

The cosmetic composition may be prepared into any formulation commonly prepared in the art, e.g., solutions, suspensions, emulsions, pastes, gels, creams, lotions, powders, oils, powdered foundations, emulsion foundations, wax foundations, and sprays, without being limited thereto. More particularly, the cosmetic composition may be formulated into sun creams, emollient lotions, astringent lotions, nourishing lotions, nourishing creams, massage creams, essences, eye creams, mask packs, sprays, or powders.

When the cosmetic composition is formulated into pastes, creams, or gels, the carrier may be animal oil, plant oil, wax, paraffin, starch, tragacanth, cellulose derivatives, polyethylene glycol, silicone, bentonite, silica, talc, zinc oxide, or the like.

When the cosmetic composition is formulated into powders or sprays, the carrier may be lactose, talc, silica, aluminum hydroxide, calcium silicate, or polyamide powder. Particularly, in the form of sprays, the cosmetic composition may further include a propellant such as chlorofluorohydrocarbon, propane/butane, or dimethyl ether.

When the cosmetic composition is formulated into solutions or emulsions, the carrier may be a solvent, a solubilizer, or an emulsifier, e.g., water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

When the cosmetic composition is formulated into suspensions, the carrier may be a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum methahydroxide, bentonite, agar, and tragacanth.

The present disclosure also provides a health functional food for preventing or alleviating skin aging or a health functional food for alleviating wrinkles, each including HAPLN1 protein or an effective agent for promoting the expression or activating the functions of HAPLN1 protein, as an active ingredient.

The health functional food may further include hyaluronic acid.

The health functional food may be provided in the form of powders, granules, tablets, capsules, syrups, or drinks, and the health functional food may be used appropriately according to any known method in combination with any other food or food additives in addition to the HAPLN1 protein or the effective agent according to the present disclosure used as the active ingredients. The amount of the active ingredient to be mixed therewith may be appropriately determined according to purposes thereof, e.g., prevention, health, or treatment.

Effective doses of the HAPLN1 protein and the effective agent contained in the health functional food may be adjusted in accordance with effective dose of the pharmaceutical composition. However, when prolonged intake is intended for the purpose of health and hygiene, the effective doses may be below the above range. In addition, since there is no safety problem, the active ingredient may be used in an amount above the range.

Types of the health functional food are not particularly limited and examples of the health functional food may include meats, sausages, breads, chocolates, candies, snacks, cookies, pizzas, ramens, other noodles, gums, dairy products including ice creams, various kinds of soups, beverages, teas, drinks, alcoholic beverage, and vitamin complexes.

Mode of Disclosure

Hereinafter, the present disclosure will be described in more detail according to the following examples. However, the following examples are merely presented to exemplify the present disclosure, and the scope of the present disclosure is not limited thereto. Example of the present disclosure

<Example 1> Search for Intrinsic Factor of Skin Aging

Heterochronic parabiosis is an experiment of connecting blood vessels of an old mouse and a young mouse of the same species to share blood. A heterochronic parabiosis experiment model is used to search for and identify an internal factor causing aging of nerves, hearts, and muscles in living organisms.

Thus, to confirm the presence of the internal factor related to skin aging in living organisms, an old C57BL/6J mouse aged 20 months purchased from the Korea Basic Science Institute and a young C57BL/6J mouse aged 6 weeks purchased from Central Lab Animal Inc. were anesthetized and skins and abdominal muscles of the mice obtained by incision were joined together by parabiosis. In case of the young mouse, skin was incised from a right forepaw to a right hindlimb by about 5 cm and then right abdominal muscles were incised by about 1 cm. In case of the old mouse, skin was incised from a left forepaw to a left hindlimb by about 5 cm and then left abdominal muscles were incised by about 1 cm. The incised abdominal muscles and skins were joined and sutured for parabiosis. After the mice were maintained for 3 weeks and euthanized, plasma and skin tissue were collected from the mice of each group. A total amount of blood was collected by orbital blood collection and incubated in an ethylenediaminetetraacetic acid (EDTA)-coated blood collection tube for about 30 minutes and then centrifuged at a rate of 10,000×g to separate plasma. The separated plasma was stored at −70° C. As skin tissue, cervical skin was collected from the mice to a size of 1 cm×1 cm after hair removal.

For immunofluorescence, the collected skin tissue was fixed in 10% (v/v) formalin to prepare a paraffin section. The prepared slide was deparaffinized and rehydrated and then stained by immunofluorescence using goat anti-mouse pro-collagen type I α2 (COL1A2) polyclonal IgG (Santa Cruz Biotechnology) and donkey anti-goat IgG(H+L) Alexa Fluor 594 (Life technologies) antibody.

For qRT-PCR, the separated skin tissue was cultured overnight in 0.25% (w/v) trypsin/EDTA at 4° C., and then the dermal layer was separated therefrom and total mRNA was extracted using a TRIzol reagent. From the extracted mRNA, cDNA was synthesized by using a cDNA synthesis kit (Life technologies). Then, proCOL1A1, proCOL1A2, proCOL3A1, and GAPDH were quantified by qRT-PCR (quantitative reverse transcription-polymerase chain reaction).

As a result, as shown in FIGS. 1A, 1B, 2A, and 2B, it was confirmed that productions of collagen (FIGS. 1A and 1B) and hyaluronic acid (FIGS. 2A and 2B) were increased in skin tissue of the old mouse (YO-O) in the heterochronic parabiotic pair of the old mouse O and the young mouse Y, when compared with that of the old mouse (OO-O) in the isochronic parabiotic pair of the old mouse O and the old mouse O.

Thus, it was confirmed that there may be an intrinsic factor related to skin aging in living organisms.

Figure 3:
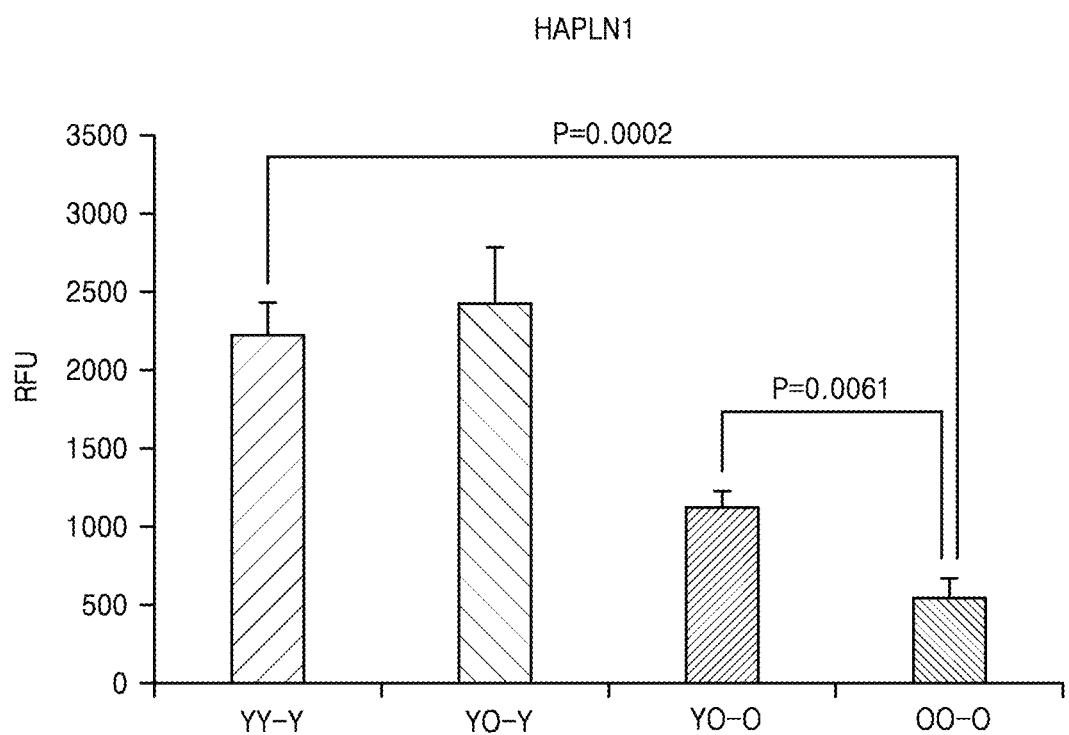
FIG. 3 shows results confirming that an intrinsic factor related to skin aging is HAPLN1.

In addition, plasma was isolated from the mice of each experiment and intrinsic factor was identified by SomaScan proteomics (SomaLogic, Inc.). As a result, HAPLN1 was identified as a protein related to aging as shown in FIG. 3.

<Example 2> Identification of Quantitative Decrease of HAPLN1 by Skin Aging 1. Decrease in Collagen Production by Skin Aging Cervical skin tissue was collected from an old male C57BL/6J mouse aged 20 months and a young male C57BL/6J mouse aged 6 months to a size of 1 cm×1 cm and total mRNA was extracted therefrom in the same manner as in Example 1. From the extracted mRNA, cDNA was synthesized by using a cDNA synthesis kit and then amounts of mRNA of pro-collagen type I (proCOL1A1 and proCOL1A2) and type III (proCOL3A1) were quantified by qRT-PCR.

Figure 4A:
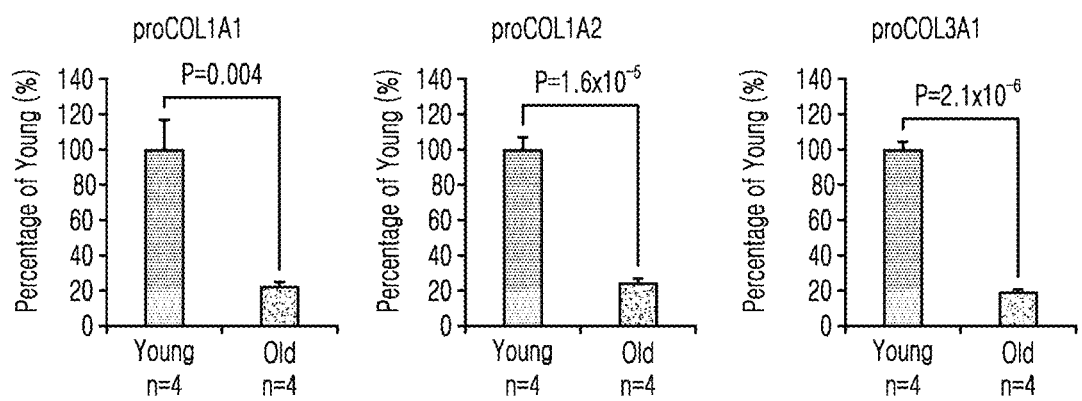
FIGS. 4A and 4B show results of comparing amounts of mRNA of pro-collagen and distributions of pro-collagen between skins of old mice and young mice.

As a result, as shown in FIG. 4A, the mRNA levels of proCOL1A1, proCOL1A2 and proCOL3A1 in the old mouse decreased to 1/4.3, 1/4.2, and 1/5.6, respectively, when compared with those of the young mouse.

Figure 4B:
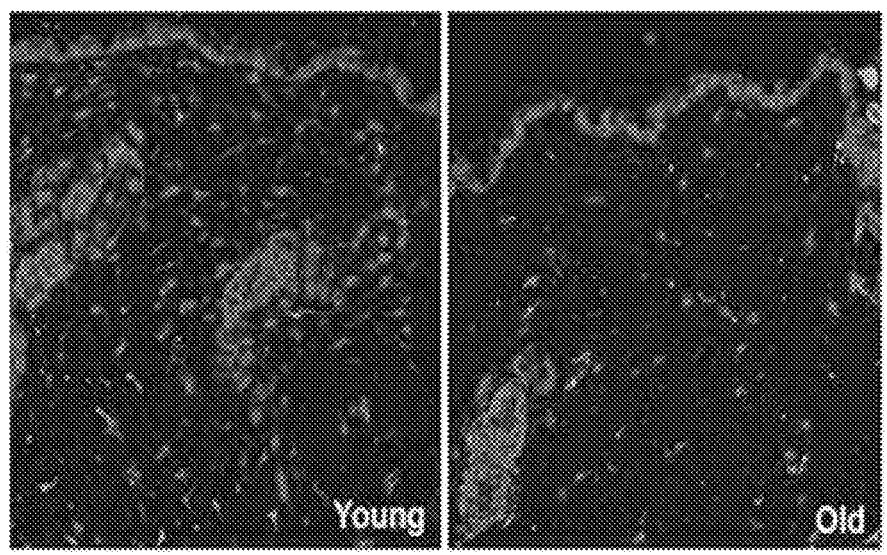

In addition, a paraffin section was prepared using the cervical skin tissue collected from the old mouse and the young mouse and stained by immunofluorescence in the same manner as in Example 1. As a result of observation using a confocal microscope, it was confirmed that distribution of the pro-collagen type I decreased in the skin of the old mouse as shown in FIG. 4B.

2. Decrease in Amount of Hyaluronic Acid by Skin Aging

Cervical skin tissue was collected from an old male C57BL/6J mouse aged 20 months and a young male C57BL/6J mouse aged 6 months to a size of 1 cm×1 cm in the same manner as in Example 1 and subjected to enzyme-linked immunosorbent assay (ELISA). First, subcutaneous fat was removed from the separated skin tissue using a blade and the skin tissue was homogenized in a phosphate buffer saline (PBS) solution supplemented with a 1× protease inhibitor. Hyaluronic acid was quantified according to manufacturer's instructions using a hyaluronic acid ELISA kit (CUSABIO).

Figure 5A:
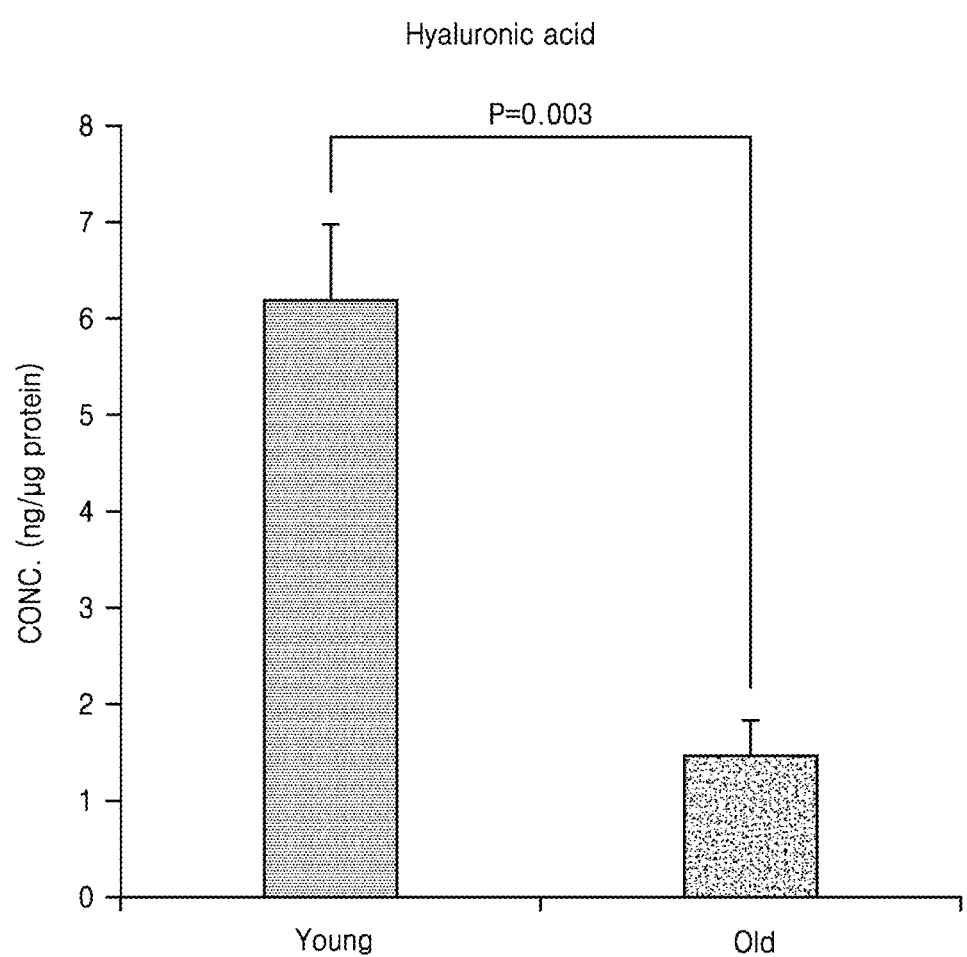
FIGS. 5A and 5B show results of comparing concentrations and distributions of hyaluronic acid between skins of old mice and young mice.

As a result, the concentration of hyaluronic acid in the old mouse decreased to about 1/4.2 of that in the young mouse as shown in FIG. 5A.

Figure 5B:
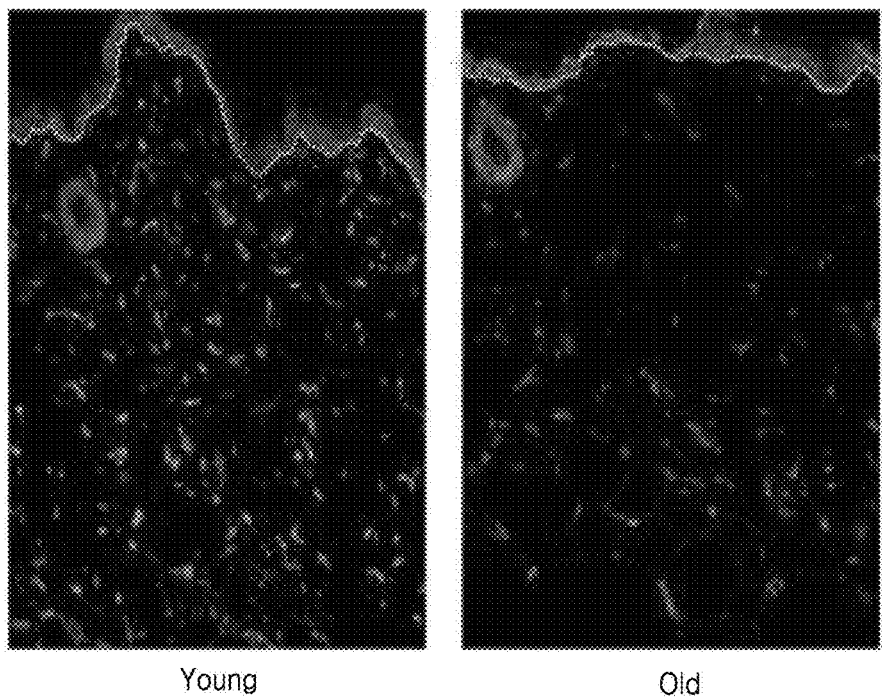

Skin tissue slices of the old mouse and the young mouse were stained by immunofluorescence in the same manner as in Example 1. In this case, sheep anti-hyaluronic acid polyclonal antibody (Abcam) and donkey anti-sheep IgG H&L Alexa Fluor 488 (Abcam) were used as anti-hyaluronic acid antibodies. As a result of observation using a confocal microscope, it was confirmed that distribution of hyaluronic acid decreased in the skin of the old mouse as shown in FIG. 5B.

3. Decrease in Expression Level of HAPLN1 by Skin Aging

Cervical skin tissue was collected from an old male C57BL/6J mouse aged 20 months and a young male C57BL/6J mouse aged 6 months and homogenized in a PBS solution in the same manner as in Example 2-2 described above, and then the concentration of HAPLN1 was measured using a mouse HAPLN1 ELISA kit (CUSABIO).

Figure 6A:
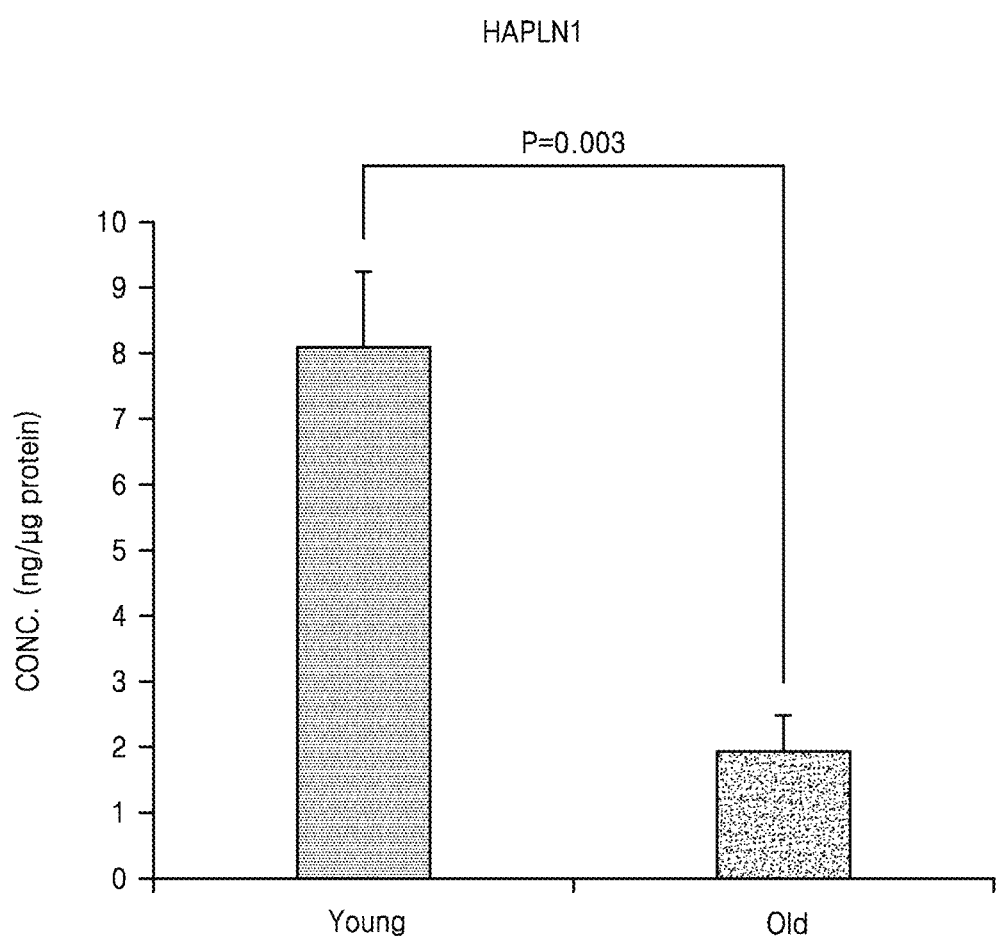
FIGS. 6A and 6B show results of comparing concentrations and distributions of HAPLN1 between skins of old mice and young mice.

As a result of measurement, the concentration of HAPLN1 decreased in the old mouse to 1/4.2 of that in the young mouse as shown in FIG. 6A.

Also, skin tissue slices of the old mouse and the young mouse were stained by immunofluorescence in the same manner as in Example 1. In this case, goat anti-HAPLN1 polyclonal IgG (Santa Cruz Biotechnology) and donkey anti-goat IgG(H+L) Alexa Fluor 594 (Life technologies) were used.

Figure 6B:
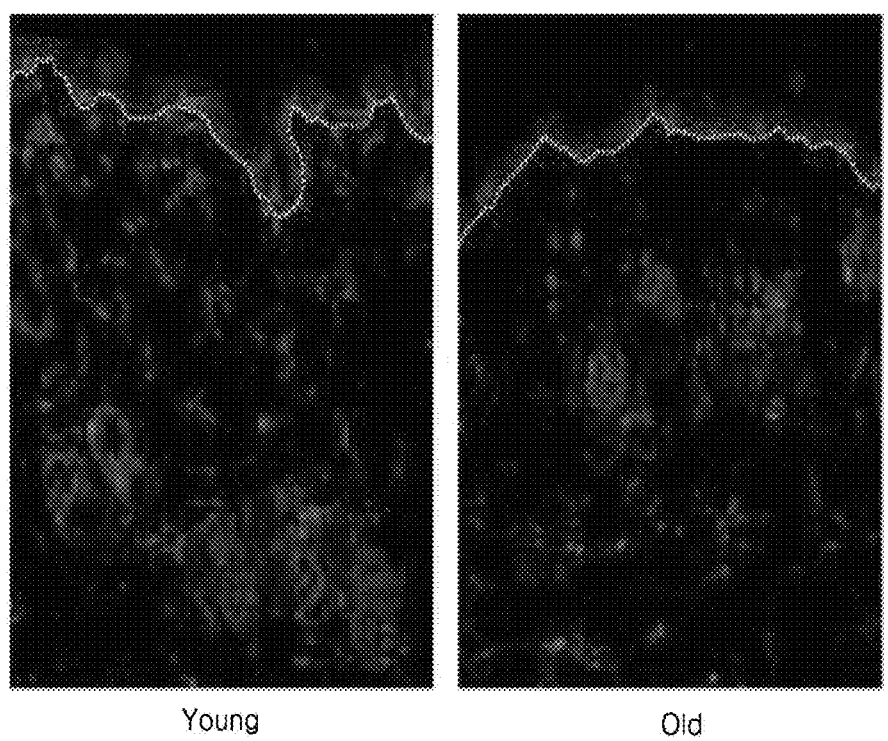

As a result of observation using a confocal microscope, it was confirmed that distribution of HAPLN1 decreased in the skin of the old mouse as shown in FIG. 6B.

<Example 3> Identification of Effects of Administration of HAPLN1 on Alleviating Skin Aging Recombinant mouse HAPLN1 (purchased from Cusabio Biotech Co) was dissolved in PBS and administered to an old male C57BL/6J mouse aged 20 months via an intraperitoneal route at a dose of 0.1 mg/kg once a day for 14 days. The same amount of PBS was administered to an old mouse and a young mouse (aged 6 months) to prepare control groups for comparison therebetween.

1. Identification of Increase in Collagen in Old Mouse by Administration of HAPLN1

After completion of the administration, the dermal layer was separated from skin tissue of each of the experimental group and the control groups in the same manner as in Example 1 and RNA was extracted therefrom to quantify pro-collagen type I (proCOL1A1 and proCOL1A2) and type III (proCOL3A1) by qRT-PCR.

Figure 7A:
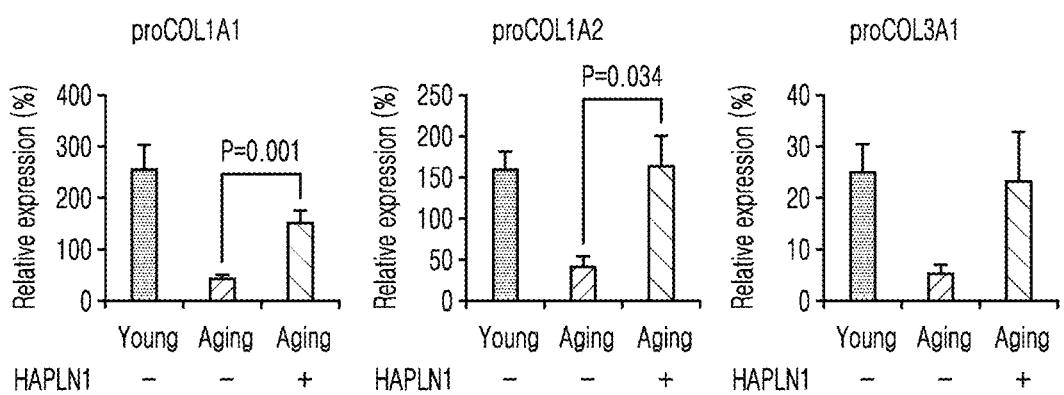
FIGS. 7A and 7B show results of identifying increases in collagen in old mice by administration of HAPLN1.
Figure 7B:
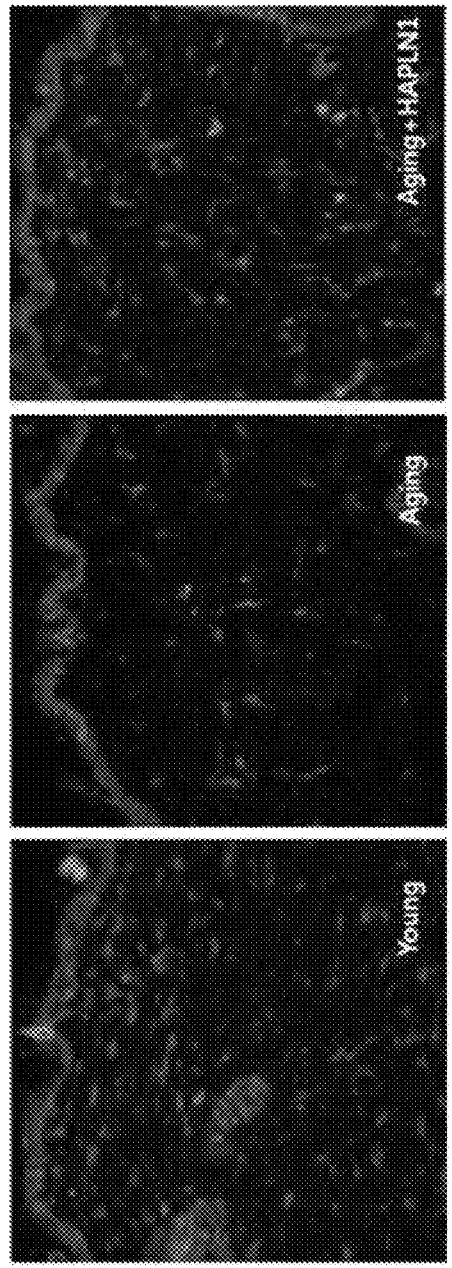

As a result, as shown in FIG. 7A, it was confirmed that the mRNA levels of the proCOL1A1, proCOL1A2 and proCOL3A1 increased by 2.6 times, 2.5 times, and 2.8 times, respectively, in the HAPLN1-administered group, when compared with the non-administration group, indicating restoration to a level similar to that of the young mouse. In addition, the skin tissue slices were stained by anti-pro-collagen type I antibody and observed using a confocal microscope in the same manner as in Example 2-1. As a result, it was confirmed that distribution of the pro-collagen type I in the HAPLN1-administered group increased to a level similar to that of the young mouse as shown in FIG. 7B.

2. Identification of Increase in Hyaluronic Acid in Old Mouse by Administration of HAPLN1

After completion of the administration, cervical skin tissue was collected from each of the experimental group and the control groups and homogenized in a PBS solution in the same manner as in Example 2-2, and then hyaluronic acid was quantified using a hyaluronic acid ELISA kit (CUSABIO) according to manufacturer's instructions.

Figure 8A:
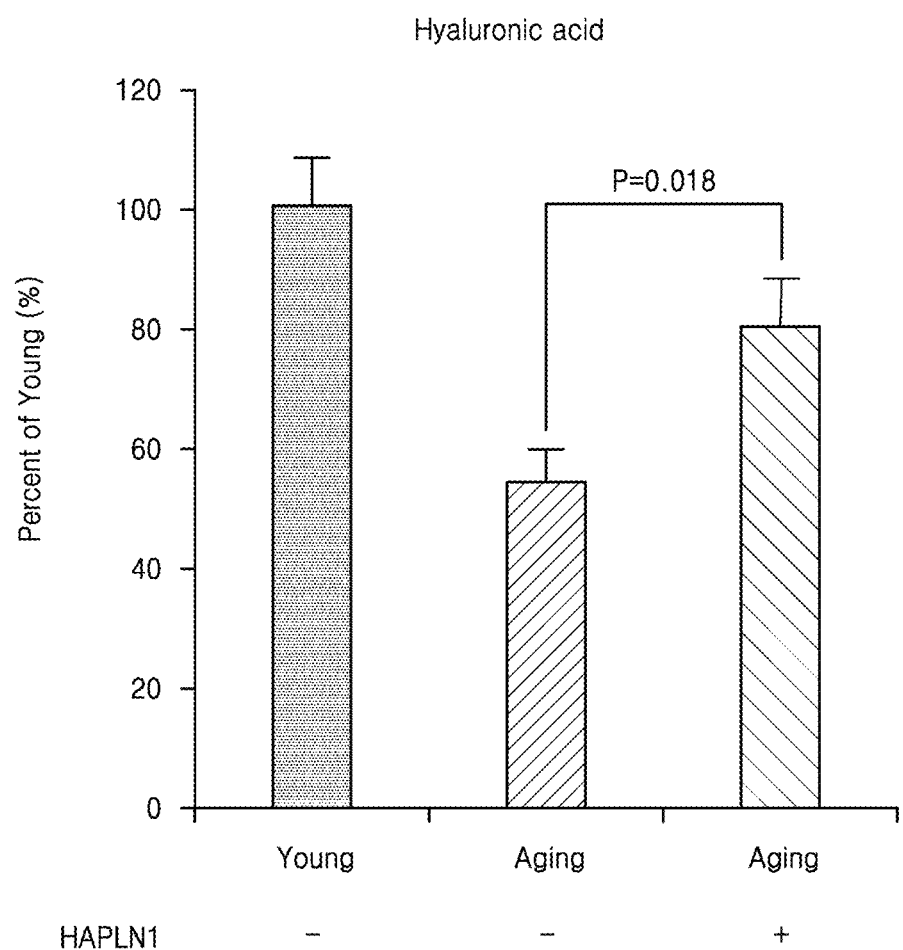
FIGS. 8A and 8B show results of identifying increases in hyaluronic acid in old mice by administration of HAPLN1.

As a result, as shown in FIG. 8A, it was confirmed that the amount of hyaluronic acid increased in the HAPLN1-administered group by 1.5 times, when compared with the non-administration group, indicating restoration to a level similar to that of the young mouse.

Figure 8B:
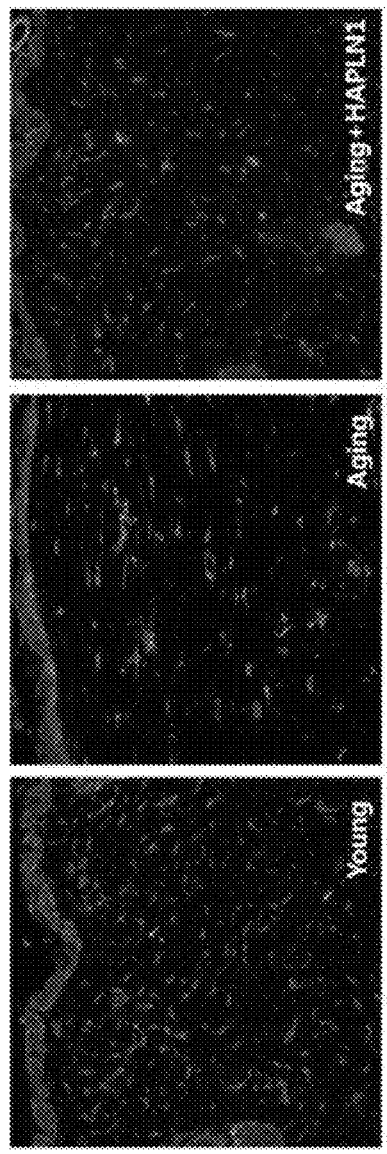

In addition, hyaluronic acid in the skin tissue slices was stained by immunofluorescence in the same manner as in Example 2-2 and observed using a confocal microscope. As a result, it was confirmed that distribution of hyaluronic acid increased in the HAPLN1-administered group to a level similar to that of the young mouse, when compared with the non-administration group, as shown in FIG. 8B.

<Example 4> Identification of Increase in TGF-β1 Receptor II, TGF-β1-Induced Collagen Production, and Hyaluronic Acid Synthesis Enzyme (HAS2) by HAPLN1 Treatment 1. Identification of Increase in TGF-β1-Induced Collagen Production in NHDF Cell by HAPLN1 Treatment Normal human dermal fibroblast (NHDF) cell lines were subjected to western blotting assay to identify whether HAPLN1 affects TGF-β1-induced proCOL1α2 production. TGF-β is a factor inducing production of collagen. At 30 minutes after NHDF cell lines were treated with different concentrations of recombinant human HAPLN1 (rhHAPLN1) (0, 25, 50, and 100 ng/ml), the NHDF cell lines were treated with 1 ng/ml of recombinant human TGF-β1 for 24 hours.

Figure 9:
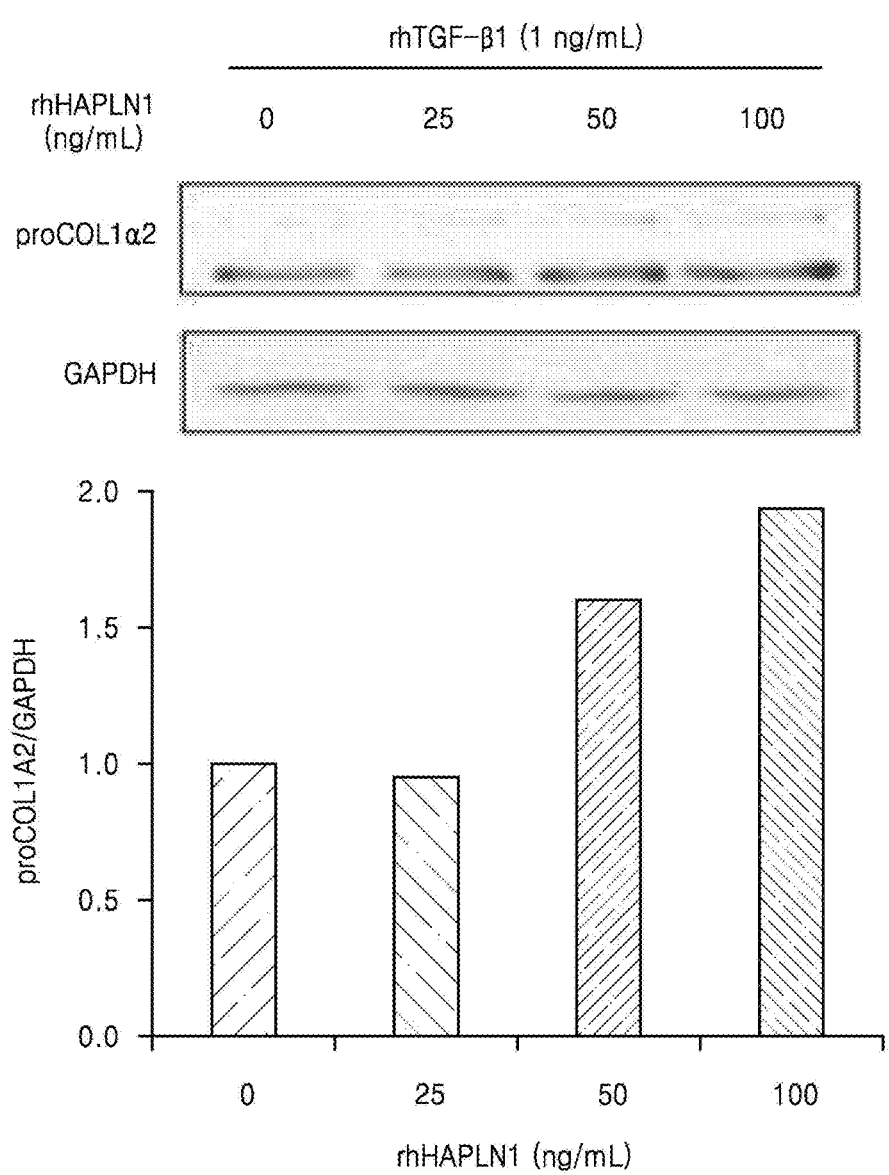
FIG. 9 shows results of identifying increases in TGF-β-induced collagen in normal human dermal fibroblast (NHDF) cells by HAPLN1 treatment.

As a result, it was confirmed that TGF-β1-induced proCOL1α2 production increased by HAPLN1 treatment as shown in FIG. 9.

2. Identification of Increase in TGF-β Receptor II in NHDF Cell by HAPLN1 Treatment To identify whether HAPLN1 affects TGF-β signaling, NHDF cell lines were treated with different concentrations of recombinant human HAPLN1 (rhHAPLN1) (0, 25, 50, and 100 ng/ml). After 24 hours, protein expression levels of TGF-β receptors were measured by western blotting.

Figure 10A:
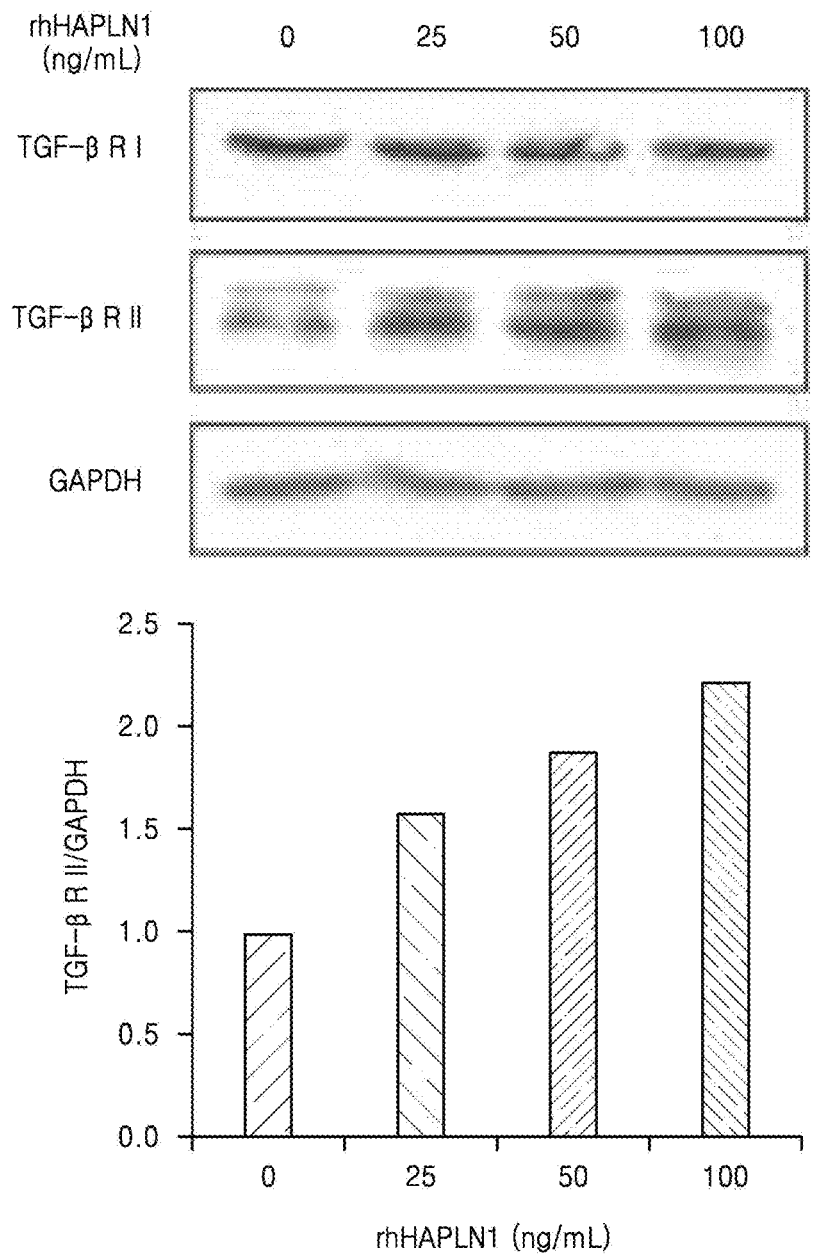
FIGS. 10A to 10C show results of identifying increases of expression levels of TGF-β receptor II protein in collagen synthesis signaling pathways in NHDF cells by HAPLN1 treatment.
Figure 10B:
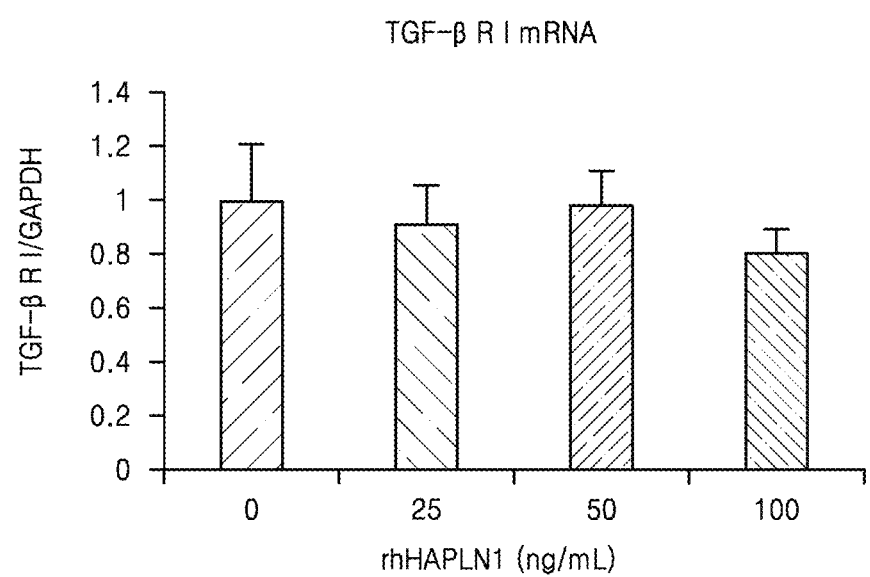
Figure 10C:
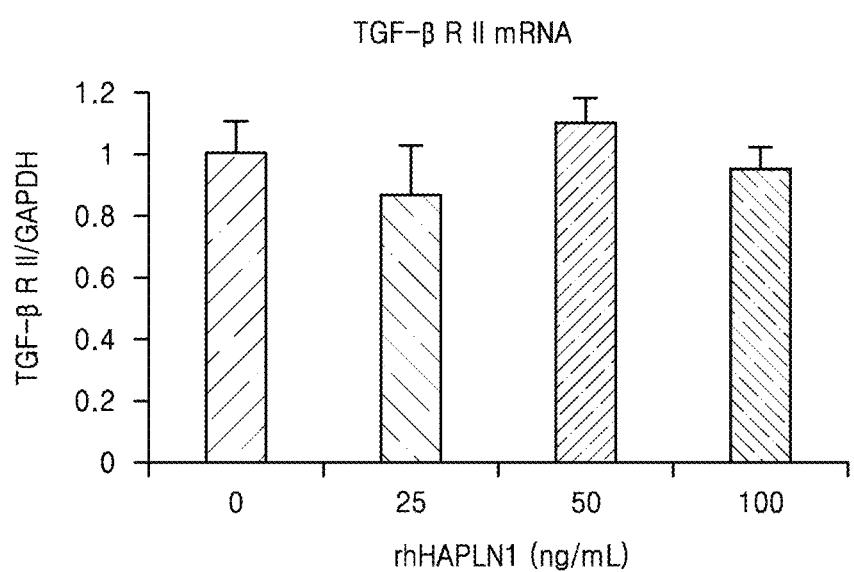

As a result, it was confirmed that the protein expression level of TGF-β receptor II between the two types of receptors as shown in FIG. 10A increased in a concentration-dependent manner by HAPLN1 treatment. As a result of measuring mRNA expression levels of the TGF-β receptors by qRT-PCR under the same conditions, it was confirmed that there was no difference by HAPLN1 treatment as shown in FIGS. 10B and 10C.

Thus, to identify whether HAPLN1 increased the amount of the TGF-β receptor II by regulation of stability instead of transcriptional regulation, the cells, which were pre-treated with cycloheximide as a protein synthesis inhibitor at a concentration of 10 μM for 1 hour, were treated with 100 ng/ml rhHAPLN1 for 6 hours or 24 hours, and protein expression levels of the TGF-β receptor II were identified by western blotting.

Figure 11:
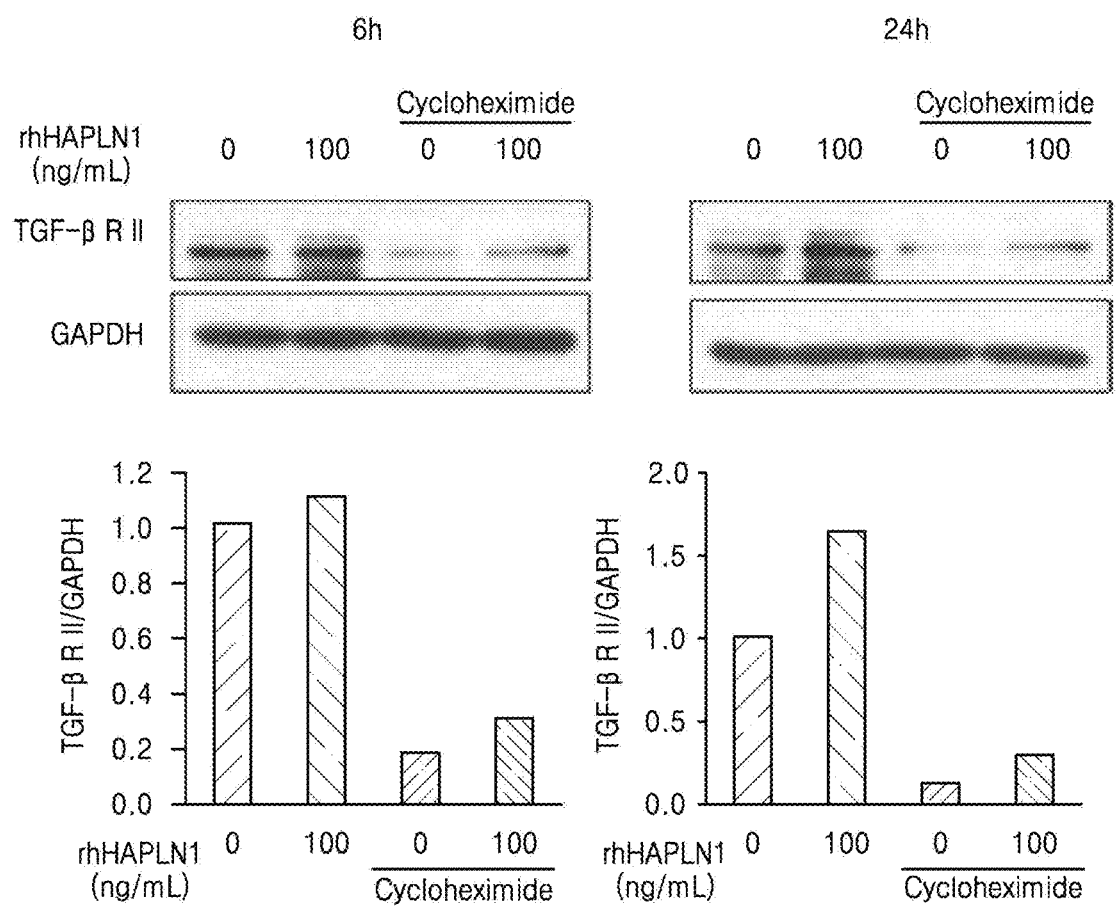
FIG. 11 shows results of identifying an increase in stability of TGF-β receptor II in NHDF cells by HAPLN1 treatment.

As a result, it was confirmed that the amount of TGF-β receptor II increased by rhHAPLN1 treatment even in the presence of cycloheximide as shown in FIG. 11. Thus, it can be seen that HAPLN1 increases the stability of the TGF-β receptor II.

3. Identification of Increase of Expression of TGF-β1-Induced Hyaluronic Acid Synthase (HAS2) in NHDF Cell by HAPLN1 Treatment In dermal fibroblasts, hyaluronic acid synthase 2 HAS2 mainly exists among three types of hyaluronic acid synthases HAS1, HAS2, and HAS3. To identify whether HAPLN1 affects expression of TGF-61-induced HAS2 in NHDF cell lines, at 30 minutes after the NHDF cell lines were treated with different concentrations of recombinant human HAPLN1 (rhHAPLN1) (0, 25, 50, and 100 ng/mL), the NHDF cell lines were treated with 1 ng/mL of recombinant human TGF-61 for 24 hours and the protein expression levels of HAS2 were identified by western blotting.

Figure 12:
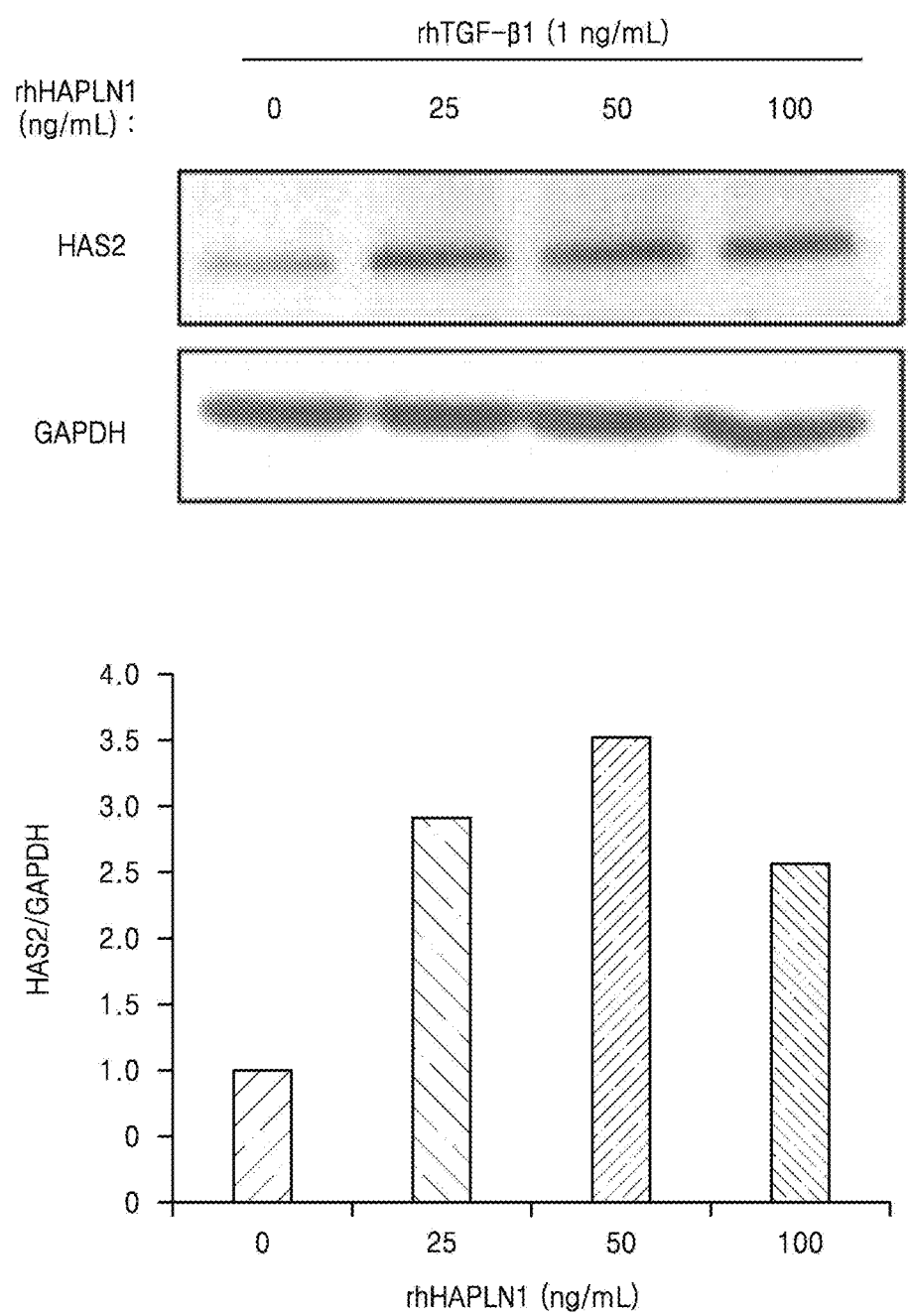
FIG. 12 shows results of identifying an increase in the expression level of TGF-β-induced hyaluronic acid synthase 2 (HAS2) protein in NHDF cells by HAPLN1 treatment.

As a result, it was confirmed that the expression level of TGF-61-induced HAS2 increased by HAPLN1 treatment as shown in FIG. 12.

The above description of the disclosure is provided for the purpose of illustration, and it would be understood by those skilled in the art that the above-described embodiments of the disclosure are illustrative in all aspects and do not limit the disclosure. Therefore, the scope of the disclosure is defined by the following claims and their equivalents rather than by the detailed description of the illustrative embodiments.

We claim:

1. A method for alleviating skin aging in a subject, comprising:
   administering a composition comprising HAPLN1 protein as an active ingredient to the subject.

2. The method of claim 1, wherein the skin aging is wrinkle formation.

3. The method of claim 1, wherein the skin aging is wrinkle formation caused by a decrease in dermal extracellular matrix.

4. The method of claim 1, wherein the composition further comprises hyaluronic acid.

5. The method of claim 1, further comprising administering hyaluronic acid to the subject.

6. The method of claim 1, wherein the composition is administered to the subject by oral or parenteral administration.

7. The method of claim 1, wherein the composition is a pharmaceutical composition or a cosmetic composition.

\* \* \* \* \*